United States Patent [19]

Ito

[11] 4,274,594

[45] Jun. 23, 1981

[54] FOAM GENERATING AND DISPENSING DEVICE

[75] Inventor: Kazuo Ito, Kamakura, Japan

[73] Assignee: Toyo Seikan Kaisha Ltd., Tokyo, Japan

[21] Appl. No.: 858,082

[22] Filed: Dec. 6, 1977

[51] Int. Cl.[3] .......................... B65D 1/32; B05D 7/30; A61M 11/02

[52] U.S. Cl. .................................... 239/327; 239/343; 239/345; 239/370; 222/189

[58] Field of Search ............... 239/327, 343, 345, 370; 222/189, 211, 212

[56] References Cited

U.S. PATENT DOCUMENTS 3,709,437 1/1973 Wright ................................ 239/327

4,022,351 5/1977 Wright ................................ 239/343

4,027,789 6/1977 Dickey ................................ 239/343

*Primary Examiner*—Robert B. Reeves

*Assistant Examiner*—Brian Bond

*Attorney, Agent, or Firm*—Charles E. Brown

[57] ABSTRACT

A squeeze type foamed liquid dispensing device comprising a squeeze container, an inner cap threaded on the container and defining a mixing chamber receiving a secondary porous foaming member thereabout, a check valve chamber, an air intake port and an air discharge tube receiving portion, an outer or cover cap releasably fitted on the inner cap for normally closing the air intake port and having a foamed liquid jet orifice and an air discharge tube received in the air discharge tube receiving portion of the inner cap and having a primary porous foaming member thereabout.

8 Claims, 4 Drawing Figures

FOAM GENERATING AND DISPENSING DEVICE

BACKGROUND OF THE INVENTION

Field of the Invention

This invention relates to a foamed liquid dispensing device.

In a prior art foamed liquid dispensing device, a fine screen mesh is interposed between the outlet in the mixing chamber where a foamable liquid and air are mixed together to provide a foamed liquid and the jet orifice in the squeeze container so that the foamed liquid can be dispensed through the orifice as a fine mist. However, the prior art foamed dispensing device of the type has the disadvantages that the amount of the foamed liquid to be dispensed varies greatly depending upon the magnitude of squeezing force to be applied to the container, that the rising extent of foam can not be maintained constant throughout the squeezing operation and is often insufficient and that the dispensing rate of the foamed liquid can not be regulated.

SUMMARY OF THE INVENTION

Therefore, one principal object of the present invention is to provide a squeeze type foamed liquid dispensing device which always dispenses substantially the same amount or rate of foamed liquid under squeezing force regardless of the type of the foamable liquid held in the container and the squeezing force applied to the container.

Another object of the present invention is to provide a squeeze type foamed liquid dispensing device in which the amount or rate of a foamed liquid to be dispensed can be simply and easily regulated by replacing its parts with corresponding parts of different sizes and shapes.

The above and other objects and attendant advantages of the present invention will be more readily apparent to those skilled in the art from a reading of the following detailed description in conjunction with the accompanying drawings which show preferred embodiments of the present invention for illustration purpose only, but not for limiting the scope of the same in any way.

PREFERRED EMBODIMENTS OF THE INVENTION

Figure 1:
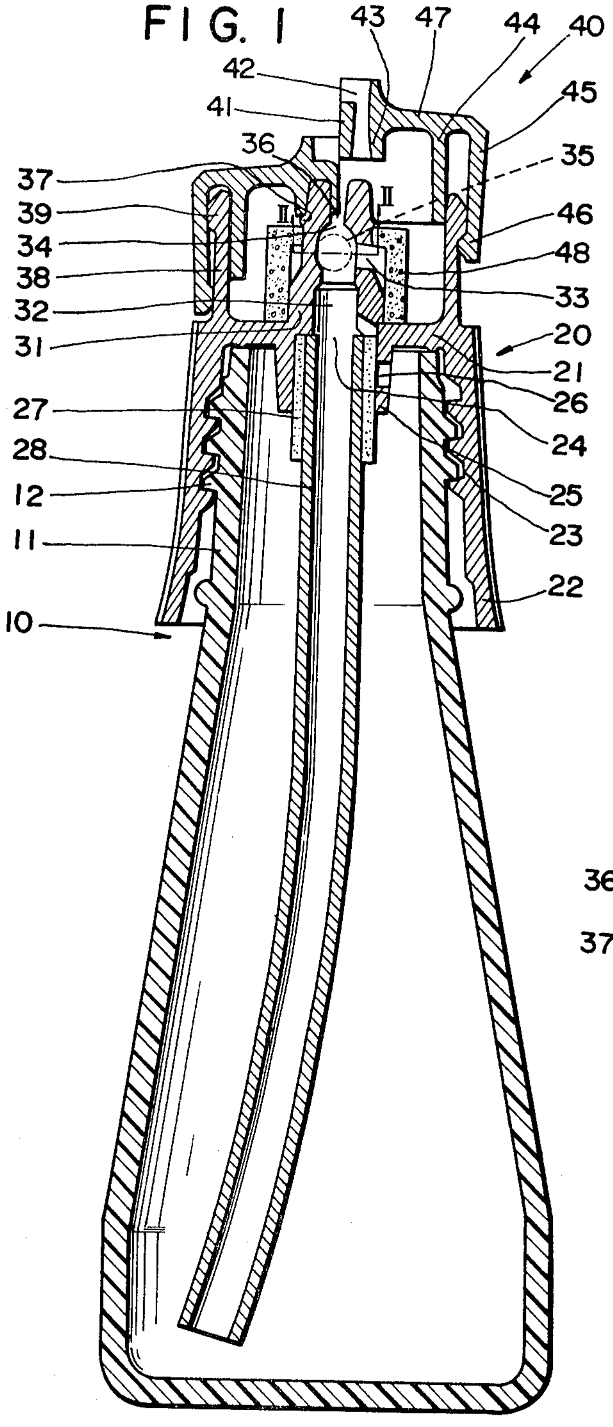
FIG. 1 is a vertically sectional view of a first embodiment of squeeze type foamed liquid dispensing device constructed in accordance with the present invention showing the upper left-hand portion in its operative or open position.

The present invention will now be described referring to the accompanying drawings and more particularly, to FIGS. 1 and 2 thereof in which the first embodiment of squeeze-type foamed liquid dispensing device of the invention is shown. The dispensing device comprises a frusto-conical flexible squeeze container formed of thermoplastic synthetic resin and generally shown by reference numeral 10 and the container is provided in its outer periphery of the upper portion thereof with a male threaded portion 12. A first or inner cap 20 having a female threaded portion 23 on the inner surface of its skirt 22 is threaded on the container with the female threaded portion 23 in threaded engagement with the male threaded portion 12 of the container. The inner cap 20 further has an integral annular member 21 extending horizontally across the hollow interior of the inner cap in a position between the upper and lower ends of thereof and having a center through hole 24 of relatively large diameter, a first cylindrical member 25 extending integrally and downwardly from the annular member 21 and having the inner diameter greater than the diameter of the through hole 24. The cylindrical member 25 is provided with a foamable liquid ingress port 26 in its wall.

A second or inner cylindrical member 31 extends integrally and upwardly from the annular member 21 in coaxial relationship to the through hole 24 and has an inner diameter which is at least as great as that of the hole 24. The second cylindrical member 31 defines a mixing chamber 32 therein in the lowermost portion thereof, a check valve chamber 34 positioned just above the mixing chamber 32 and having the diameter smaller than that of the mixing chamber and a smallest diameter air intake port 36 in the uppermost portion of the cylindrical member 31. As is more clearly shown in FIG. 2, the wall portion of the second cylindrical member 31 which defines the mixing chamber 32 is provided with a discharge port 33 having a suitable size.

A third or outer cylindrical member 38 extends integrally and upwardly from the periphery of the annular member 21 in coaxial and peripherally spaced relationship to the second or inner cylindrical member 31 and has a radially and outwardly extending bulge 39 on the outer surface adjacent to the upper end of the associated cylindrical member.

An air discharge tube 28 having a tubular primary foaming member 27 thereabout is received in the first cylindrical member 25 with a lower portion of the tube extending beyond the lower end of the cylindrical portion and a portion of the porous member exposed to the ingress port 26 in the first cylindrical member 25.

A tubular secondary porous foaming member 48 surrounds the second or inner cylindrical member 31 with a portion of the porous member filling up the discharge port 33 which is in communication with the mixing chamber 32 defined in the cylindrical member 31.

The tubular secondly porous foaming member 48 is mounted on the second cylindrical member 31 by an outwardly extending bulge 37 which is formed on the outer surface of middle portion of the second or inner cylindrical member 31.

A check valve 35 is received within the check valve chamber 34 defined in the second or inner cylindrical member 31.

A second or cover cap 40 is fitted on the first or inner cap 20 and comprises a center plug 41 adapted to close the air intake port 36 in the uppermost portion of the inner cylindrical member 31, an annular seating member 43 disposed radially and outwardly of the plug in peripherally spaced relationship thereto and an annular jet orifice 42 defined between the plug and seating member and in communication with both the air intake port 36 and the open air. The cover cap 40 also includes an inner cylindrical member 44 disposed radially and outwardly of the seating member 43 in peripherally spaced relationship to the latter to be fitted in the third or outer cylindrical member 38 of the inner cap 20 and an outer cylindrical member 45 disposed radially and outwardly of the inner cylindrical member 44 in peripherally spaced relationship to the latter. The plug 41 and inner and outer cylindrical members 44, 45 extend integrally and downwardly from the common top 47 of the cover cap 40 whereas the seating member 43 extends integrally and upwardly and downwardly from the top 47 of the cover cap 40. The outer cylindrical member 45 of the cover cap 40 is provided on the inner surface adjacent to the lower end thereof with a bulge 46 adapted to engage the bulge 39 on the third or outer cylindrical member 38 of the inner cap 20.

When the assembly comprising the first or inner cap 20 and second or cover cap 40 having the above-mentioned construction and arrangement is placed in a predetermined position on the mouth 11 of the container 10, the plug 41 of the outer cap 40 closes the air intake port 36 in the inner cap 20 and the seating member 43 of the cover cap 40 of the inner cap 20 fits on the upper portion of the second or inner cylindrical member 31 to close the jet orifice 42.

With the above-mentioned construction and arrangement of the parts of the squeeze-type foamed liquid dispensing device of the invention, in operation, the cover cap 40 is first pulled upwardly from the inner cap 20 until the bulge 46 on the outer cylindrical member 45 of the cover cap 40 engages the bulge 39 on the outer cylindrical member 38 of the inner cap 20 whereby the cover cap is prevented from being inadvertently removed from the inner cap and the air intake port 36 and jet orifice 42 are uncovered. Then, when the container 10 is turned upside down, the check valve 35 falls down to close the air intake port 36 at the inner end of the port to thereby prevent the foamable liquid held in the container 10 from escaping through the air intake port. Thereafter, the container 10 is squeezed or an external pressure is applied thereto and as a result, the air which is now accumulating at the now bottom of the inverted container is forced to flow upwardly through the air discharge tube 28 into the mixing chamber 32 and at the same time, the foamable liquid held within the container 10 permeates and passes through the primary porous foaming member 27 into the mixing chamber 32 to mix with the air therein. While passing through the porous member 27, the liquid is transformed into a liquid comprising large bubbles particles and upon entering the mixing chamber 32, the bubbles mix with the air to cause foam to further rise in the liquid. At this time, since the check valve 35 closes the air intake port 36 under the squeezing force or external pressure applied to the container 10, the foamed liquid intrained in the air is forced to flow toward and through the discharge port 33. As the air-entrained foamed liquid flows from the mixing chamber 32 to and through the discharge port 33, the foamed liquid permeates and passes through the tubular secondary porous foaming member 48, the bubbles are reduced in size to provide a foamed liquid comprising fine foam of bubbles of substantially uniform size and the resulting foamed liquid then passes to and through the jet orifice 42 from where the uniformly foamed liquid is dispensed. Thereafter, when the container 10 is released from the squeezing force or external pressure, a negative pressure develops in the flexible container 10 to push the check valve 35 upwardly away from the air intake port 36 to thereby allow the air intake port to communicate with the outer air whereupon the outer air is sucked into the interior of the container 10.

By repeating the container squeezing operation as mentioned hereinabove, a desired amount of the foamed liquid is dispensed out of the dispensing device each time the container is squeezed.

When the foamable liquid is dispensed in a foamed liquid state out of the container of the dispensing device of the invention mentioned hereinabove, the liquid is transformed into coarse foam particles as the liquid passes the primary foaming porous member 27, the coarsely foamed liquid is transformed into a finely foamed liquid as the liquid passes from the mixing chamber 32 to and through the secondary foaming porous member 48 and the finely foamed liquid comprises substantial portion of fine foams of substantially uniform size. Thus, the foamed liquid can be dispensed out of the dispensing device of the invention as a foamed liquid comprising foam of finer and more uniform size bubbles as compared with the foamed liquid dispensed out of the conventional foamed liquid dispensing devices.

In the conventional foam liquid dispensing device similar to the dispensing device of the invention mentioned hereinabove except that the first porous member 27 of the invention is not provided, the foamable liquid flows directly into the mixing chamber in its air-liquid mixing state or aerosol state and therefore, even after the foamable liquid has permeated and passed through the porous foaming member associated with the mixing chamber so as to cause foams to rise therein, the resulting foamed liquid does not comprise bubbles of fine and uniform size.

On the other hand, according to the present invention, even when a very high squeezing force or external pressure is applied to the container, since the foamable liquid held within the container is first forced to permeate and pass through the primary foaming porous member 27 into the mixing chamber 32 and the flow of foamable liquid is subjected to high resistance by the porous member 27 as the liquid passes through the porous member, there is no possibility that any excess amount of the foamable liquid flows into the mixing chamber 32 under such high squeezing force and thus, dispensing of the foamed liquid in any excess amount can be effectively prevented.

And when it is desired to dispense the foamed liquid in a relatively small amount each time, it is only necessary to employ a relatively low porosity or high mesh porous member as the primary porous foaming member 27 to thereby increases the resistance to the flow of the foamable liquid through the porous member.

And according to the present invention, when the foamable liquid to be held within the container has a relatively high viscosity, it is only necessary that a high porosity or lower mesh porous member be employed as the primary porous foaming member 27 to thereby offer a relatively low resistance to the flow of the foamable liquid through the porous member. By the employment of such high porosity porous member, the same amount of foamed liquid of high viscosity can be dispensed out of the dispensing device as of the foamed liquid of lower viscosity with the same squeezing force.

Furthermore, according to the present invention, when it is desired to obtain a foamed liquid comprising bubbles finer and more uniform size, it is only necessary that a porous foaming member having the porosity suitable for causing such foams to rise as the secondary porous member 48.

Figure 3:
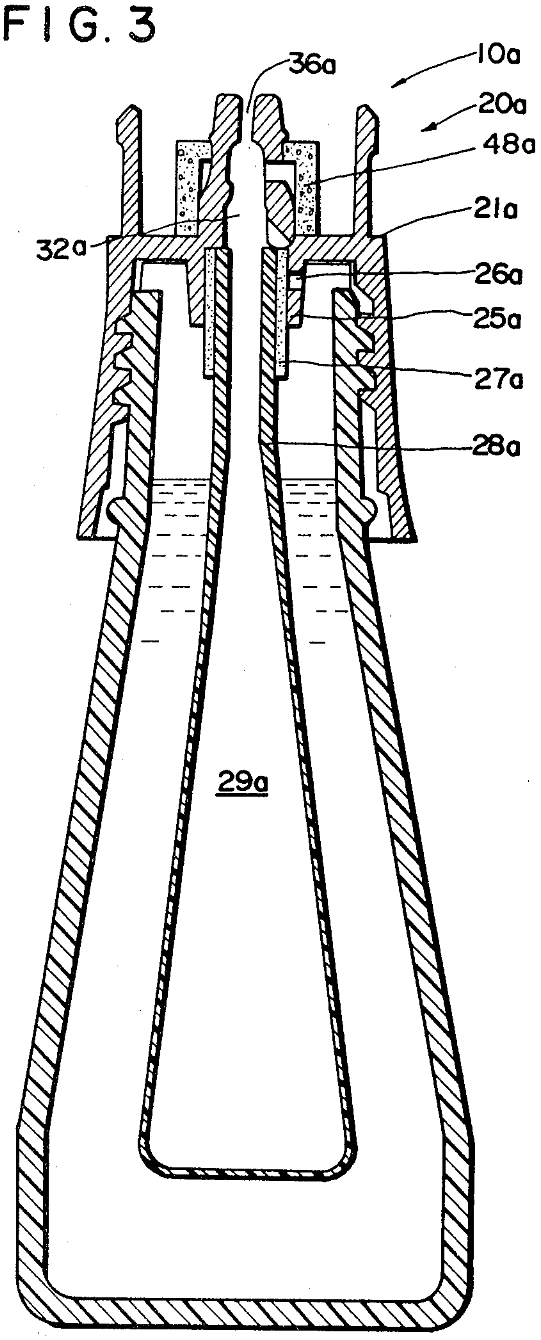
FIGS. 3 and 4 are vertically sectional views of modified embodiments of squeeze-type foamed liquid dispensing device constructed in accordance with the present invention.

Turning now to FIG. 3 of the accompanying drawings in which the second embodiment of foamed liquid dispensing device of the invention is shown with the cover cap removed therefrom. In FIG. 3, the parts of the device which correspond to those of the first embodiment are assigned the same numerals thereto and description will be made of only the parts which are modified and associated with the modified parts. As shown in FIG. 3, the first cylindrical member 25*a* extending integrally and downwardly from the annular member 21 of the inner cap 20*a* receives the air discharge tube 28*a* having an air bag 29*a* connected to the lower end thereof and the primary porous foaming member 27*a* thereabout. When the container 10*a* of the dispensing device FIG. 3 is squeezed or an external pressure is applied thereto, the foamable liquid held within the container 10*a* is forced to flow through the ingress port 26*a* in the cylindrical member 25*a* and permeate and pass through the primary foaming porous member 27*a* into the mixing chamber 32 and at the same time, the air trapped in the air bag 29*a* also flows through the air discharge tube 28*a* into the mixing chamber 32*a* to mix with the in-flowing foamable liquid therein. The arrangement of FIG. 3 has advantages over the prior art squeeze-type foamed liquid dispensing device in that the air discharge tube 28*a* has no air bag 29*a* connected thereto. When the container of the prior art foamed liquid dispensing device is squeezed for a first dispensing operation, the foamable liquid held within the discharge tube 28*a* is first forced to flow into the mixing chamber 32*a* and thus, the mixing chamber 32*a* is filled with the foamable liquid which has passed through the ingress port 26*a* in the cylindrical member 25*a* and the foamable liquid from the discharge tube 28*a* which contains no air therein. Although the foamable liquid mixture may include a certain amount of bubbles therein after the liquid has passed through the secondary foaming porous member 48*a* 37, when dispensed, the dispensed liquid contains a substantial amount of liquid component. On the other hand, by the provision of the air bag 29*a* as shown in the embodiment in FIG. 3, when the container 10 is turned upside down and squeezed, the air within the air bag 29*a* is forced to flow through the discharge tube 28*a* into the mixing chamber 32*a*, and therefore, only the air is positively forced to flow into the mixing chamber 32*a* when the container is squeezed initially. In this way, the foamed liquid comprising bubbles of desired uniform density can be dispensed by the initial squeezing without the disadvantages that the the foamed liquid comprising a substantial portion of liquid component is dispensed in the initial squeezing operation as experienced in the prior art foamed liquid dispensing device.

When the container is released from the squeezing force, a negative pressure developes in the container and the outer air is of course allowed to flow through the air intake port 36*a* into the air bag 29*a*.

Figure 2:
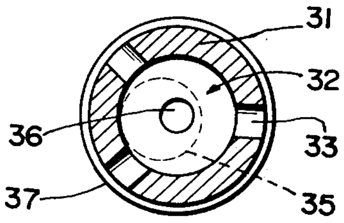
FIG. 2 is a cross-sectional view of the upper portion of the inner cylindrical member of the inner cap of said squeeze-type foamed liquid dispensing device as shown in FIG. 1.

In the first and second embodiments, as shown in FIGS. 1, 2 and 3, the air discharge tube 28 having the liquid permeable porous member 27 thereabout is received in the cylindrical member 25 positioned below the air mixing chamber 32, but the present invention is not limited to such arrangement of the air discharge tube and porous member.

Figure 4:
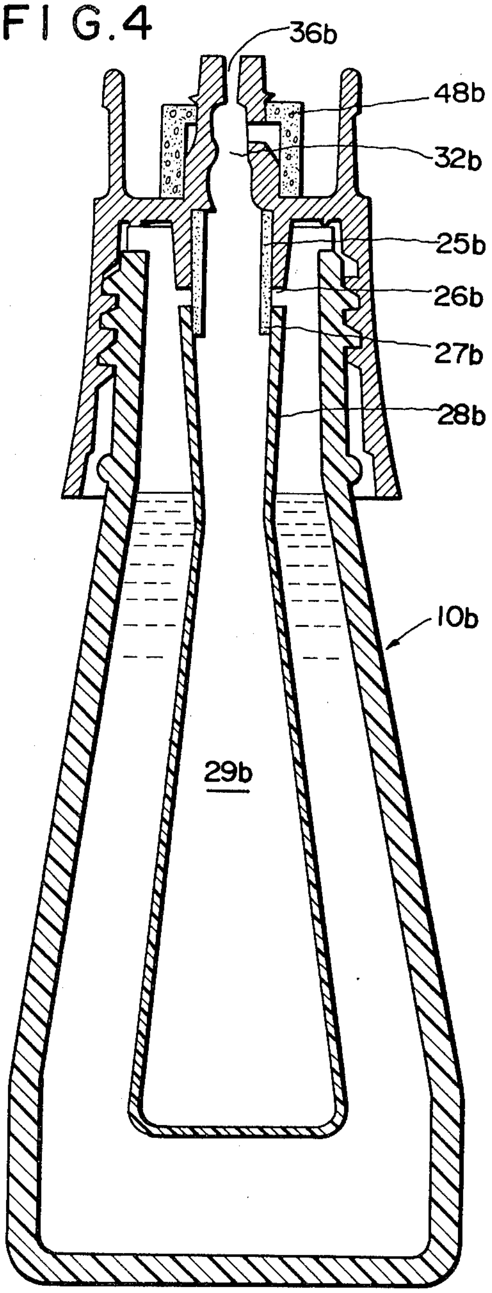

In the modified embodiment of FIG. 4, a porous cylindrical member 25*b* is positioned right below the mixing chamber 32*b* and has a liquid ingress portion 26*b* and a primary porous foaming portion 27*b* positioned right below the portion 26*b*. Thus, it will be appreciated that various changes may be made on the construction and arrangement of the cylindrical member 25*b*, ingress port 26*b*, primary porous foaming member 27*b*, secondary porous foaming member 48*b* and discharge tube 28*b* within the scope of the invention.

While several embodiments of the invention have been shown and described in detail it will be understood that the same are for illustration purpose only and are not to be taken as a definition of the invention, reference being had for this purpose to the appended claims.

What is claimed is:

1. A squeeze-type foamed liquid dispensing device comprising a flexible container, an inner cap threaded on said container and defining a mixing chamber, a check valve chamber and an air intake port above said mixing chamber, an outer cap releasably fitted on said inner cap and defining a jet orifice in communication with said mixing chamber for receiving foamed liquid therefrom, an air discharge tube depending from said inner cap and opening directly into said mixing chamber, and a porous foaming member attached to said inner cap and also opening directly into said mixing chamber.

2. The squeeze-type foamed liquid dispensing device as set forth in claim 1, in which said inner cap includes an annular member extending horizontally across the inner cap and having a center through hole, a first cylindrical member extending downwardly from the center of said annular member in coaxial relationship to said center through hole, a second cylindrical member extending upwardly from the center of said annular member in coaxial relationship to said center hole and defining said mixing chamber, check valve chamber and air intake port and a third cylindrical member extending upwardly from the periphery of said annular member in peripherally spaced relationship to said second cylindrical member and having a bulge on the outer surface thereof; and said outer cap includes a horizontal top, a plug extending downwardly from the center of said top for closing said air intake port, a seating member disposed radially and outwardly of said plug in peripherally spaced relationship thereto for fitting on said second cylindrical member of the inner cap, said plug and seating member defining said jet orifice therebetween, an outer cylindrical member being disposed radially and outwardly of said seating member in peripherally spaced relationship thereto and having a bulge on the inner surface for engaging said bulge on the third cylindrical member of the inner cap.

3. The squeeze-type foamed liquid dispensing device as set forth in claim 2, in which a second porous foaming member is disposed about said second cylindrical member of the inner cap.

4. A squeeze-type foamed liquid dispenser comprising a closure for a container, said closure including a transverse partition wall for forming a seal with a container mouth, an air discharge tube depending from said partition wall, a tubular wall above said partition wall defining a mixing chamber in direct communication with said air discharge tube, and a tubular porous foaming member disposed concentric with said air discharge tube and having an upper end surface opening directly into said mixing chamber, said air discharge tube and said tubular porous foaming member for directly admitting air and foamed liquid into said mixing chamber, an air inlet into said mixing chamber, and a check valve between said air inlet and said mixing chamber for preventing discharge of foamed liquid out through said air inlet.

5. A squeeze-type foamed liquid dispenser comprising a closure for a container, said closure including a transverse partition wall for forming a seal with a container mouth, an air discharge tube depending from said partition wall, a tubular wall above said partition wall defining a mixing chamber in direct communication with said air discharge tube, and a tubular porous foaming member disposed concentric with said air discharge tube and having an upper end surface opening directly into said mixing chamber, said air discharge tube and said tubular porous foaming member for directly admitting air and foamed liquid into said mixing chamber, said partition wall having a depending tube portion, and said tubular porous foaming member being telescoped around said air discharge tube and within said tube portion, said tube portion has at least one liquid inlet therethrough opening into an intermediate external part of said tubular porous foaming member.

6. A squeeze-type foamed liquid dispenser comprising a closure for a container, said closure including a transverse partition wall for forming a seal with a container mouth, an air discharge tube depending from said partition wall, a tubular wall above said partition wall defining a mixing chamber in direct communication with said air discharge tube, and a tubular porous foaming member disposed concentric with said air discharge tube and having an upper end surface opening directly into said mixing chamber, said air discharge tube and said tubular porous foaming member for directly admitting air and foamed liquid into said mixing chamber, a second tubular porous foaming member surrounding said mixing chamber, and said mixing chamber having at least one discharge passage opening into said second tubular porous foaming member.

7. A dispenser according to claim 6 together with an overcap defining a second chamber surrounding said second tubular porous foaming member, said overcap defining a jet orifice for dispensing foamed liquid, said jet orifice being in communication with said second chamber.

8. A dispenser according to claim 7 together with cooperating closure means in said overcap and said closure for closing said jet orifice.

* * * * *